United States Patent [19] … [11] Patent Number: 4,996,320
Umemoto et al. … [45] Date of Patent: Feb. 26, 1991

[54] N-FLUOROPYRIDINIUM SALT AND PROCESS FOR PREPARING SAME

[75] Inventors: Teruo Umemoto; Kyoichi Tomita, both of Sagamihara; Kosuke Kawada, Hon; Ginjiro Tomizawa, Wako, all of Japan

[73] Assignee: Sagami Chemical Research Center, Japan

[21] Appl. No.: 296,411

[22] Filed: Jan. 9, 1989

Related U.S. Application Data

[63] Continuation of Ser. No. 22,275, Mar. 5, 1987, abandoned, which is a continuation-in-part of Ser. No. 870,010, Jun. 3, 1986, abandoned.

[30] Foreign Application Priority Data

Jun. 3, 1985 [JP] Japan .................................. 60-118882
Mar. 7, 1986 [JP] Japan .................................... 61-48450

[51] Int. Cl.$^5$ .................... C07F 9/58; C07D 491/048; C07D 219/04; C07D 213/55
[52] U.S. Cl. .......................................... 546/9; 546/22; 546/116; 546/102; 546/153; 546/155; 546/157; 546/168; 546/170; 546/180; 546/286; 546/287; 546/321; 546/326; 546/345; 546/346; 546/347
[58] Field of Search ................ 546/345, 321, 326, 347, 546/346, 9, 22, 102, 153, 155, 157, 168, 170, 180, 286, 287

[56] References Cited

FOREIGN PATENT DOCUMENTS 0204535 12/1986 European Pat. Off. ............ 546/345

OTHER PUBLICATIONS

March, Advanced Organic Chemistry, Reactions, Mechanisms and Structure, Second Edition, pp. 460–468 McGraw–Hill Publishers 1977.
Umemoto et al., Chem. Abstracts, vol. 106, (15), Abst. No., 106:119,640f, Apr. 13, 1987.
"The Chemistry of Heterocyclic Compounds a Series of Monographs" Arnold Weissberger, Consulting Editor.
Vol. 14, Pyridine and Its Derivatives, Parts 1–4, ed by Erwin Clingsbert, 1960 (Part 1), 1961 (Part 2), 1962 (Part 3), 1964 (Part 4) Interscience Publishers, Inc., New York.
Vol 14, Pyridine and Its Derivatives, Supplement Parts 1–4, ed by R. A. Abramovitch, 1974 (Part 1-3, 1975 (Part 4), John Wiley & Sons, Inc., New York.
Vol 14, Pyridine and its Derivatives, Supplement Part 5, ed by George R. Newkome, 1984, John Wiley & Sons, Inc. New York.

*Primary Examiner*—Alan L. Rotman
*Attorney, Agent, or Firm*—Olson & Hierl

[57] ABSTRACT

A pyridine-compound is reacted with fluorine together with a Bronsted acid-compound or Lewis acid to form a N-fluoropyridinium salt which is very active to other compounds but is very selective for the preparation of a desired product and this product is very useful for a fluorine-introducing agent which makes it useful for the preparation of fluoro-compounds such as thyroid inhibitor.

5 Claims, No Drawings

N-FLUOROPYRIDINIUM SALT AND PROCESS FOR PREPARING SAME

This application is a continuation of application Ser. No. 022,275, filed Mar. 5 1987, now abandoned, which was a continuation-in-part application of Ser. No. 870,010, filed June 3, 1986, now abandoned.

BACKGROUND OF THE INVENTION

The present invention relates to a N-fluoropyridinium salt and a process for preparing same. The N-fluoropyridinium salts according to the present invention are very useful as a fluorine atom introducing agent as seen from the examples 66–133 hereinafter illustrated. The salts according to the invention have a widespread use because of their high reactivity with a wide variety of compounds and selectivity for any desired products. For example, said salt can be used for the preparation of 3-fluoro-4-hydroxyphenylacetic acid which is useful as a thyroid inhibitor by reacting the former with p-hydroxyphenylacetate followed by a common hydrolysis reaction as illustrated in examples 79 to 82 referred to hereinafter.

Heretofore, it has been well known in the art that fluorine compounds are significantly distinguished from chlorine compounds, bromine compounds, and iodine compounds in their physical properties and reactivities, because fluorine atom have characteristics such as very high electronegativity, high ionization energy, extremely high bonding ability with other atoms, small Van der Waals diameter, lack of a d-electron orbit and the like (N.Ishikawa & Y.Kobayashi; FLUORINE COMPOUNDS; THEIR CHEMISTRY AND APPLICATIONS; KodanshaSchientific, PP. 69–70,1979). Therefore, fluorination reactions naturally have significantly different aspects from other halogenation reactions such as chlorinations, brominations and iodinations.

In reactions with organic compounds, fluorine, contrary to chlorine, bromine and iodine, reacts very violently, readily giving rise to the fission of the C—C bond of organic compounds and in cases where the reaction is excessively violent, fire or explosion in turn can break out. The abnormality of fluorination reactions relative to other halogenation reactions may be readily understood from the comparison of heat of formation in halogenation reactions (see the description on pages 69–75 of the above article) as follows:

| type of reaction | ΔH (Kcal/mol) | | | |
|---|---|---|---|---|
| | X = F | Cl | Br | I |
| C=C + $X_2$ → CX—CX | −111 | −36 | −23 | −16 |
| C—H + $X_2$ → C—X + HX | −105 | −25 | −9 | +6 |

As seen from the above Table, since the heat of reaction in the fluorination reactions amounts to ever 100 Kcal/mol, while the bonding energy between carbon-carbon atoms is approximately only 60 Kcal/mol, the control of fluorination reactions is very difficult, contrary to other halogenation reactions. Accordingly, the development of fluorination reactions having better selectivity has been an important subject matter in fluorination industries.

For the purpose resolving the above problem, a wide variety of compounds for introducing fluorine atoms have heretofore been studied and developed. As such compounds, for example, trifluoromethyl-hypofluorite ($CF_3OF$), trifluoroacetyl-hypofluorite ($CF_3COOF$), acetylhypofluorite ($CH_3COOF$), xenon difluoride ($XeF_2$), $FClO_3$, sulfur tetrafluoride ($SF_4$), diethylaminosulfur trifluoride ($Et_2NSF_3$), $CClHFCF_2NEt_2$, $CF_3CFHCF_2NEt_2$, heavy metal fluorides such as AgF, HgF, $CoF_3$, $AgF_2$ and the like were known in the art (see pages 79–94 of the above-mentioned article). However, these compounds have drawbacks such as poor selectivity for the desired reaction, are highly hazardous to handle, have high cost, unstableness, a limited scope of application, and the like which make them commercially unsatisfactory. On the other hand, hydrogen fluoride, hydrofluoric acid, potassium fluoride, cesium fluoride, and the like which are known as inexpensive agents for introducing fluorine atoms are inferior in electrophilic reactivity, which imposes such limitations that they cannot perform electrophilic substitutions for aromatic nuclei or negatively charged carbon ions. These compounds also present serious problems in handling because hydrogen fluoride or hydrofluoric acid, for example, are highly toxic. It has been suggested that a pyridine. $F_2$ complex can be used as a fluorine atom-introducing agent, but it can only offer low total yield of fluorination reactions [see, Z. Chem., 12, 292 (1972)] and moreover, said complex is highly hygroscopic and thermally unstable so that explosions may break out at above −2° C. [Z. Chem., 5, 64 (1965)]. From the above, it can hardly be said that the complex is a useful fluorinating agent. Recently, N-fluoro-N-alkylarenesulfoneamide have been reported as fluorine atom-introducing agents, but these compounds are low in reactivity and only effective for particular reaction species (negatively charged carbon ions) [J. Amer. Chem. Soc. 106, 452 (1984)]. Therefore, a strong need exists for the development of highly satisfactory fluorine atom-introducing agents.

As a result of a series of earnest investigations by the present inventors towards the development of a novel fluorine-introducing agent, they have succeeded in developing a novel fluorine-introducing agent which is active but stable allowing the easy handling of the agent which still retains high selectivity for a desired reaction, thus completing the present invention. The compounds according to the present invention have high reactivity with a variety of compounds and high selectivity for any desired compounds, which allows the compounds to be very useful for the synthesis of a variety of fluorine-containing compounds in a shortened process. For example, a thyroid inhibitor, 3-fluoro-4-hydroxyphenylacetic acid could easily be prepared from p-hydroxyphenylacetate available industrially (see, Examples 79–82 hereinafter described).

SUMMARY OF THE INVENTION

The present invention relates to a N-fluoropyridinium salt represented by the formula:

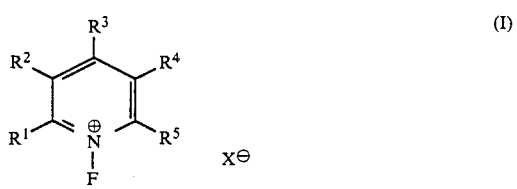

(I)

wherein $R^1$, $R^2$, $R^3$, $R^4$ and $R^5$ represent a hydrogen atom, a halogen atom, an alkyl, aryl, acyl, alkoxycarbonyl, aryloxycarbonyl, carbamoyl, nitro, cyano, alkylsulfonyl, arylsulfonyl, hydroxy, alkoxy, aryloxy, acyloxy, acylthio, amido, alkanesulfonyloxy, or arenesulfonyloxy group; $X\ominus$ represents a conjugate base of Bronsted acid except for $F\ominus$, $Cl\ominus$, $Br\ominus$ and $I\ominus$ which are conjugate bases of hydrogen halides; and $R^1$, $R^2$, $R^3$, $R^4$ and $R^5$ may be combined together directly or through a hetero atom or atoms in a variety of combinations to form a cyclic structure, while $X\ominus$ may be combined directly or through a hetero-atom or atoms with $R^1$, $R^2$, $R^3$, $R^4$ and $R^5$ in various combinations.

The present invention further relates to a process for producing the above N-fluoropyridinium salt by reacting a pyridine-compound having the general formula:

wherein $R^1$ to $R^5$ represent the same meaning as defined above, with fluorine ($F_2$) and a Bronsted acid compound having the general formula:

XM    (III)

wherein M represents a hydrogen atom, a metal atom, an ammonium residue, a pyridinium residue or a group $SiR^6R^7R^8$ in which $R^6$, $R^7$ and $R^8$ are an alkyl, aryl, alkoxy, aryloxy, acyloxy group, or a halogen atom; and X represents the same meaning as above.

DETAILED DESCRIPTION OF THE INVENTION

The pyridine-compounds set forth in formula (II) employable in the present invention are those which are easily available or which may be prepared readily and are exemplified by pyridine; straight or branched alkylated or cyclic alkylated pyridine such as methylpyridine, dimethylpyridine, trimethylpyridine, tetramethylpyridine, pentamethylpyridine, ethylpyridine, diethylpyridine, butylpyridine, dibutylpyridine, tributylpyridine, pentylpyridine, hexylpyridine, decylpyridine, (trifluoromethyl)-pyridine,bis(trifluoromethyl)pyridine, tris(trifluromethyl)-pyridine, (trichloromethyl)pyridine, (pentafluoroethyl)-pyridine, (perfluorooctyl)pyridine, (methoxymethyl)pyridine, ethyl pyridylacetate, pyridylacetonitrile, pyridylacetone, and the like; halopyridines such as chloropyridine, bromopyridine, fluoropyridine, dichloropyridine, difluoropyridine, trichloropyridine, tetrachloropyridine, pentachloropyridine, trifluoropyridine, pentafluoropyridine, chlorofluoropyridine, dichlorofluoropyridine, and so on; (trifluoromethyl)chloropyridine, (trifluoromethyl)dichloropyridine, (trifluoromethyl)trichloropyridine, (trifluoromethyl)fluoropyridine, methylchloropyridine, phenylpyridine, diphenylpyridine, triphenylpyridine, dipyridyl, acetylpyridine, bisacetylpyridine, benzoylpyridine;(alkoxycarbonyl)pyridine or (aryloxycarbonyl)pyridine such as (methoxycarbonyl)-pyridine,(ethyoxycarbonyl)pyridine,(butoxycarbonyl)pyridine, bis(ethoxycarbonyl)pyridine,bis(trifluoroethoxycarbonyl)-pyridine, tris(methoxycarbonyl)pyridine,(phenoxycarbonyl)-pyridine; 2,3-pyridinedicaboxylic anhydride,nitropyridine, cyanopyridine, dicyanopyridine, tricyanopyridine, benzenesulfonylpyridine, methylsulfonylpyridine, chlorocyanopyridine, formylpyridine, (haloformyl)pyridine, nicotinamide,picolinamide, (dimethylaminocarbonyl)pyridine, methoxypyridine, dimethoxypyridine, propoxypyridine, butoxypyridine, menthoxypyridine, trifluoromethoxypyridine, acetoxypyridine, trifluoroacetoxypyridine, phenoxypyridine, acetylthiopyridine, methanesulfonyloxypyridine, benzenesulfonyloxypyridine, acetylaminopyridine,3-hydroxypyridine, and 1,2,3,4,5,6,7,8-octahydroacridine.

As the Brønsted acid compounds represented by the formula (III), there may be mentioned the following compounds: sulfonic acids or sulfuric acids such as methanesulfonic acid, butanesulfonic acid, benzensulfonic acid, toluenesulfonic acid, nitrobenzensulfonic acid, dinitrobenzensulfonic acid, trinitrobenzensulfonic acid, trifluoromethanesulfonic acid, perfluorobutanesulfonic acid, perfluorooctanesulfonic acid, trichloromethanesulfonic acid, difluoromethanesulfonic acid, trifluoroethanesulfonic acid, fluorosulfonic acid, chlorosulfonic acid, monomethylsulfric acid, sulfuric acid, camphorsulfonic acid, bromocamphorsulfonic acid, $\Delta^4$-cholestene-3-on-6-sulfonic acid, 1-hydroxy- p-methane-2-sulfonic acid, p-sytrenesulfonic acid, $\beta$-styrenesulfonic acid, poly(p-styrenesulfonic acid), vinylsulfonic acid, poly(vinylsulfonic acid), poly(2-acrylamide-2-methyl-1-propanesulfonic acid), and a copolymer of said propanesulfonic acid with styrene, perfluoro-3,5-dioxa-4-methyl-7-octenesulfonic acid, poly(-perfluoro-3,6-dioxa-4-methyl-7-octenesulfonic acid) and a copolymer of said octenesulfonic acid with tetrafluoroethylene, and the like; phosphoric acid; nitric acid; halogen acids such as perchloric acid, perbromic acid, periodic acid, chloric acid, bromic acid, and the like; carboxylic acids such as acetic acid, formic acid, trichloro-acetic acid, trifluoroacetic acid, pentafluoropropionic acid, dichloroacetic acid, acrylic acid, poly(acrylic acid), poly-(perfluoro-3,6-dioxa-4-methyl-7-octenoic acid) and a copolymer of said octenoic acid with tetrafluoroethylene and so on; compounds resulting from hydrogen halide and Lewis acids such as $HBF_4$, $HPF_6$, $HSbF_4$, $HSbF_6$, $HAsF_6$, $HBCl_3F$, $HSiF_5$ and the like; metal salts of the above mentioned Brønsted acids; a variety of ammonium salts or pyridinium salts of the above mentioned Brønsted acids; silyl compounds resulting from the substitution of hydrogen atom or atoms of the above mentioned Brønsted acids with a group $SiR^6R^7R^8$ wherein $R^6$, $R^7$ and $R^8$ are the same as defined above, or metal bifluoride such as sodium bifluoride, for example. As the group $SiR^6R^7R^8$, there may be listed, for example, trimethylsilyl, triethylsilyl, dimethylbutylsilyl, dimethylphenylsilyl, triphenylsilyl, trihalosilyl, triacetylsilyl, triacetoxysilyl, trimethoxysilyl, triphenoxysilyl. As the metals for the metal salts of Brønsted acids reference is preferably made to alkali metals or alkaline earth metals from the aspect of ecomomy and reaction efficiency. Further, as the variety of ammonium salts or pyridinium salts, there may be mentioned ammonium salts, trimethylammonium salts, triethylammonium salts, tetraethylammonium salts, benzyltrimethylammonium salts, phenylammonium salts, dimethylphenylammonium salts, naphthylammonium salts, pyridinium salts, dimethylpyridinium salts, trimethylpyridinium salts, quinolinium salts and the like.

Of the N-fluoropyridinium salts represented by formula (I), in the case where $X\ominus$ and $R^1$, $R^2$, $R^3$, $R^4$ and $R^5$ are combined together in a variety combinations, the pyridinium compounds represented by formula (II) as the raw material include, for example, sodium pyridinesulfonate, pyridinesulfonic acid, ammonium pyridinesulfonate, potassium pyridylethylsulfonate, sodium pyridinecarboxylate and the like.

The pyridine.F$_2$ complex where X$\ominus$ represents F$\ominus$ which is the conjugate base of hydrogen halide in the N-fluoropyridinium salts has a serious drawback in that it is unstable and explodes at a temperature above $-2°$ C. and when the conjugate base is Cl$\ominus$, Br$\ominus$ or I$\ominus$ the corresponding N-fluoropyridinium salts are difficult in synthesis.

The Br$\phi$sted acid-compounds for achieving better reaction efficiencies should be equal to or in excess molar amount to that of the host material, but preferably should be an equi-molar amount from an economic viewpoint. Fluorine employed in the present invention should preferably be diluted with 50 to 99.9 % by volume of an inert gas in order to suppress any violent reactions. The diluting gas includes, by way of example, nitrogen, helium, argon, tetrafluoromethane, sulfur hexafluoride and the like.

The fluorine gas for achieving better reaction efficiencies should be used in an equi-molar or in excess molar amount to the host material. However, since the amount may vary depending upon the manner of introduction, reaction temperature, reaction solvent, reaction apparatus and so on, it may preferably be selected in amounts required for eliminating the last traces of the host material.

The reaction is preferably carried out by the sue of a solvent. As the solvent, acetonitrile, methylene chloride, chloroform, carbon tetrachloride, trichlorofluoromethane, trichlorotrifluoroethane, ethyl acetate, diethyl ether, tetrahydrofuran, and the like or a mixture thereof may be used.

A reaction temperature of $-100$ to $+40°$ C. may be selected, but the range of temperature of from $-90°$ C. to room temperature is being preferred for better reaction yields.

In carrying out the process of the present invention it is occasionally preferable for improving the reaction efficiency to employ a trapping agent such as sodium fluoride to capture hydrogen fluoride produced as a by-product.

Of the N-fluoropyridinium salts having the formula (I), N-fluoropyridinium salt having the formula

(I')

(wherein R$^1$ to R$^5$ have the same meaning as above and Y represents a Lewis acid), can be prepared by reacting the pyridine-compound represented by formula (II) with fluorine (F$_2$) and a Lewis acid having the formula

Y (IV).

The Lewis acid, the starting material set forth in formula (IV), may include, for example, boron trifluoride, boron trichloride, triacetoxyboron, tri(tgrifluoroacetoxy)boron, aluminum trifluoride, aluminum trichloride, aluminum tribromide, phosphorous trifluoride, phosphorus pentafluoride, phosphorus pentachloride, arsenic trifluoride, arsenic trichloride, arsenic pentafluoride, antimony trifluoride, antimony pentafluoride, antimony dichlorotrifluoride, silicon tetrafluoride, trimethylfluorosilane, dimethylphenylfluorosilane, sulfur trioxide, titanium tetrachloride, stannic chloride, ferric chloride, and iodine pentafluoride. Ethereal complexes of these Lewis acids may also employed without any problems. These Lewis acids may be employed in an equi-molar or in excess molar amount tot he host material (II) for achieving a better reaction efficiency, but from the standpoint of economy the equi-molar amount be preferable. The manner in which fluorine is used and the amount of fluorine to be used are similar to the above embodiment.

A reaction of the present invention is preferably carried out by using a reaction solvent. The reaction solvent may include, for example, acetonitrile, methylenechloride, chloroform, trichlorofluoromethane, trichlorofluoroethane, ethylacetate, diethylether, tetrahydrofuran or a mixture thereof.

A reaction temperature may generally be in a range of $-100+40°$ C., and preferably a range of $-90+°$ C. may be selected for a better yield.

The compounds (I) according to the present invention can be readily prepared and are in most cases stable in air at room temperature. These compounds enable the simple and selective introduction of a fluorine atom to a contemplated compound with good efficiency and therefore serve as a superior fluorine-introducing agent. Further, the compounds according to the present invention, after they have once been reacted, reproduce the pyridine-compounds or form protonic salts or silyl salts of pyridine-compounds which can readily generate the starting pyridine-compounds by neutralization or treatment with water.

The following examples will illustrate the present invention in more detail.

EXAMPLE 1

Preparation of N-fluoropyridiniumtrifluoromethanesulfonate

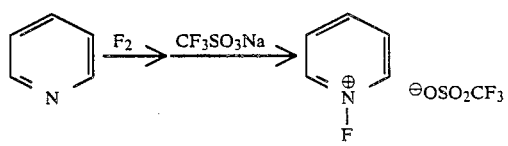

To a 50 ml trichlorofluoromethane solution containing 1.0 g (12.6 m moles) of pyridine a mixed gas of fluorine and nitrogen in a volumetric ratio of 1:9 was introduced at a rate of 30 ml/min. at $-78°$ C. under vigorous stirring. The amount of the fluorine gas introduced amounted to 34.8 mmoles. Subsequent to the fluorine introduction, 20 ml of anhydrous acetonitrile and 2.2 g (12.8 mmoles) of sodium trifluoro-methanesulfonate as a XM reactant were added to the reaction solution after which the temperature of the solution was raised to $-40°$ C., while removing the solvent with the aid of an aspirator. The solvent, after filtering sodium fluoride formed as a byproduct, was distilled off and the resultant residue was recrystallized from THF to give 1.75 g (yield: 67%) of N-fluoropyridinium trifluoromethanesulfonate, the physical properties of which are shown in Table 6.

EXAMPLE 2

Preparation of N-fluoropyridiniumtrifluoromethanesulfonate

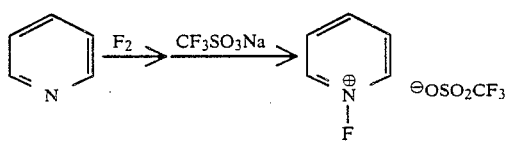

To a 100 ml anhydrous acetonitrile solution containing 10 g (0.126 mole) of pyridine a mixed gas of fluorine and nitrogen was introduced at a rate of 90 ml/min. at −40° C. under vigorous stirring. The amount of the fluorine gas introduced amounted to 0.18 mole. Subsequent to the fluorine introduction, 22 g (0.128 mole) of sodium trifluoromethanesulfonate as a XM reactant was added to the reaction solution after which the resultant reaction solution was maintained at −40° C. for 5 hours under stirring. Subsequently, the solvent, after filtering sodium fluoride, was distilled off and the resultant residue was recrystallized from methylene chloride to give 17.5 g (yield: 71%) of N-fluoropyridinium trifluoromethanesulfonate. The product thus obtained was repurified with methylene chloride/acetonitrile to recover 13.8 g (yield: 56%).

EXAMPLES 3–15

Example 3 was carried out as in Example 1 and Examples 4–15 were carried out as in Example 2. The reactants used and the results obtained are shown in Table 1 and the physical properties of the products are shown in Table 6.

Further, Example 12 employed sodium D-camphorsulfonate as the XM reactant and the angle of specific rotatory power of the product was $[\alpha]_D^{22} = +29.51$ (c=0.664, $CH_3CN$).

TABLE 1

| Example | pyridine-compound | XM | product | yield (%) |
|---|---|---|---|---|
| 3 | 3,5-dimethylpyridine | $CF_3SO_3Na$ | N-fluoro-3,5-dimethylpyridinium $\ominus OSO_2CF_3$ | 60 |
| 4 | pyridine | $NaPF_6$ | N-fluoropyridinium $\ominus PF_6$ | 34 |
| 5 | pyridine | $NaSbF_6$ | N-fluoropyridinium $\ominus SbF_6$ | 51 |
| 6 | pyridine | $NaClO_4$ | N-fluoropyridinium $\ominus ClO_4$ | 72 |
| 7 | pyridine | $CF_3SO_3H$ | N-fluoropyridinium $\ominus OSO_2CF_3$ | 44 |
| 8 | pyridine | $CF_3SO_3SiMe_3$ | N-fluoropyridinium $\ominus OSO_2CF_3$ | 45 |
| 9 | 3,5-dichloropyridine | $CF_3SO_3H$ | N-fluoro-3,5-dichloropyridinium $\ominus OSO_2CF_3$ | 41 |

TABLE 1-continued

| Example | pyridine-compound | XM | product | yield (%) |
|---|---|---|---|---|
| 10 | 3,5-dichloropyridine | CF$_3$SO$_3$SiMe$_3$ | N-fluoro-3,5-dichloropyridinium triflate | 62 |
| 11 | pyridine | FSO$_3$H | N-fluoropyridinium fluorosulfonate | 49 |
| 12 | 2,4,6-trimethylpyridine | NaOSO$_2$—(camphorsulfonate) | N-fluoro-2,4,6-trimethylpyridinium camphorsulfonate | 50 |
| 13 | 2,4,6-trimethylpyridine | FSO$_3$H | N-fluoro-2,4,6-trimethylpyridinium fluorosulfonate | 56 |
| 14 | 2,4,6-trimethylpyridine | CF$_3$COOSiMe$_3$ | N-fluoro-2,4,6-trimethylpyridinium trifluoroacetate | 77 |
| 15 | 2,4,6-trimethylpyridine | CF$_3$SO$_3$H | N-fluoro-2,4,6-trimethylpyridinium triflate | 60 |

EXAMPLE 16

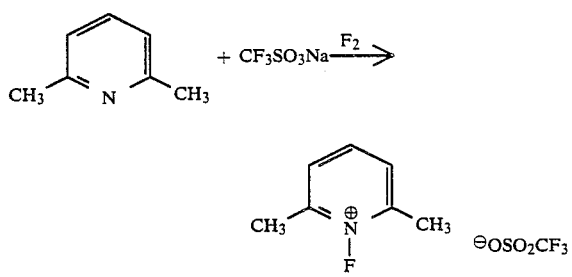

In 20 ml of anhydrous acetonitrile 0.50 g (4.67 mmoles) of 2.6- dimethylpyridine and 0.803 g (4.67 mmoles) of sodium trifluoromethanesulfonate as the XM reactant were dissolved, and to the resultant solution a mixed gas of fluorine and nitrogen (1:9) was added at a rate of 30 ml/min. at −40° C. under vigorous stirring. The amount of the fluorine gas introduced amounted to 8.93 mmoles. After the completion of the reaction, sodium fluoride was filtered and the solvent was distilled off. The resultant residue was recrystallized from THF to give 0.88 g (yield: 73%) of N-fluoro-2,6-dimethyl-pyridinium trifluoromethanesulfonate. The resultant product was further recrystallized with THF/acetonitrile to obtain 0.82 g (yield: 69%), the physical properties of which are shown in Table 6.

EXAMPLES 17-26

Examples 17-26 were carried out as in Example 16 and the results are shown in Table 2 with the physical properties in Table 6. In Example 22, 2-l-menthoxypyridine [[α]$_D^{20}$ = −110.7 (c=0.994, CHCl$_3$)] was used as the pyridine compound for the starting material and the specific rotary power of the resultant N-fluoro-2-l-menthoxypyridinium trifluoromethanesulfonate was [α]$_D^{25}$ = −77.73 (c=4.16, CHCl$_3$).

TABLE 2

| Example | Pyridine-Compound | XM | Product | Yield (%) |
|---|---|---|---|---|
| 17 | 2,4,6-trimethylpyridine | CF₃SO₃Na | N-fluoro-2,4,6-trimethylpyridinium triflate | 82 |
| 18 | 2,6-bis(methoxycarbonyl)pyridine | CF₃SO₃Na | N-fluoro-2,6-bis(methoxycarbonyl)pyridinium triflate | 72 |
| 19 | pyridine | n-C₄F₉SO₃Na | N-fluoropyridinium nonaflate | 87 |
| 20 | pyridine | CF₃SO₃Na | N-fluoropyridinium triflate | 60 |
| 21 | 2-methoxypyridine | CF₃SO₃Na | N-fluoro-2-methoxypyridinium triflate | 73 |
| 22 | 2-(menthyloxy)pyridine | CF₃SO₃Na | N-fluoro-2-(menthyloxy)pyridinium triflate | 57 |
| 23 | 3-acetoxypyridine | CF₃SO₃Na | N-fluoro-3-acetoxypyridinium triflate | 90 |
| 24 | 4-phenylpyridine | CF₃SO₃Na | N-fluoro-4-phenylpyridinium triflate | 19 |
| 25 | 2,6-bis(methoxycarbonyl)pyridine | CF₃SO₃H | N-fluoro-2,6-bis(methoxycarbonyl)pyridinium triflate | 75 |

TABLE 2-continued

| Example | Pyridine-Compound | XM | Product | Yield (%) |
|---|---|---|---|---|
| 26 | CH₃OC—[pyridine]—COCH₃ | CF₃SO₃Na | CH₃OC—[N-F pyridinium]—COCH₃ ⊖OSO₂CF₃ | 60 |

Example 27 pyridine + CF₃SO₃SiMe₃ —F₂→ N-fluoropyridinium ⊖OSO₂CF₃

To a 5 ml anhydrous acetonitrile solution containing 0.408 g (5.17 mmoles) of pyridine, 1.0 ml (5.17 mmoles) of trimethylsilyl trifluoromethanesulfonate as the XM reactant was added at −40° C. under stirring. To the resultant solution a mixed gas of fluorine and nitrogen (1:9), 10 minutes after the addition, was introduced at a rate of 15 ml/min. The amount of fluorine gas introduced was 15.5 mmoles. After the completion of the reaction, an amount of ether cooled to −60° C. was added to the solution to precipitate crystals which were filtered to give 0.99 g (yield: 78%) of N-fluoropyridinium trifluoromethanesulfonate.

EXAMPLES 28-38

Examples 28-38 were carried out as in Example 27 except that in Examples 34 the gas ratio of fluorine:nitrogen was 2.5:97.5. The results are summarized in Table 3 with the physical properties in Table 6.

TABLE 3

| Example | Pyridine-Compound | XM | Product | Yield (%) |
|---|---|---|---|---|
| 28 | pyridine | CH₃SO₃SiMe₃ | N-F pyridinium ⁻OSO₂CH₃ | 42 |
| 29 | 3,5-dichloropyridine | CF₃SO₃SiMe₃ | 3,5-dichloro-N-F pyridinium ⊖OSO₂CF₃ | 55 |
| 30 | 3-chloropyridine | CF₃SO₃SiMe₃ | 3-chloro-N-F pyridinium ⊖OSO₂CF₃ | 79 |
| 31 | 3-chloro-5-trifluoromethylpyridine | CF₃SO₃SiMe₃ | 3-chloro-5-trifluoromethyl-N-F pyridinium ⊖OSO₂CF₃ | 71 |
| 32 | 3-COOEt pyridine | CF₃SO₃SiMe₃ | 3-COOEt-N-F pyridinium ⊖OSO₂CF₃ | 69 |

TABLE 3-continued

| Example | Pyridine-Compound | XM | Product | Yield (%) |
|---|---|---|---|---|
| 33 | 3-CF$_3$, 5-Cl pyridine | CF$_3$SO$_3$SiMe$_2$Ph | N-fluoro-3-CF$_3$-5-Cl-pyridinium $^{\ominus}$OSO$_2$CF$_3$ | 71 |
| 34 | 2,6-bis(COOMe)pyridine | CF$_3$SO$_3$SiMe$_3$ | N-fluoro-2,6-bis(COOMe)pyridinium $^{\ominus}$OSO$_2$CF$_3$ | 68 |
| 35 | 3-CN pyridine | CF$_3$SO$_3$SiMe$_3$ | N-fluoro-3-CN-pyridinium $^{\ominus}$OSO$_2$CF$_3$ | 30 |
| 36 | furo[3,4-b]pyridine-5,7-dione | CF$_3$SO$_3$SiMe$_3$ | N-fluoro furo[3,4-b]pyridinium-5,7-dione $^{\ominus}$OSO$_2$CF$_3$ | 28 |
| 37 | 4-NO$_2$ pyridine | CF$_3$SO$_3$SiMe$_3$ | N-fluoro-4-NO$_2$-pyridinium $^{\ominus}$OSO$_2$CF$_3$ | 52 |
| 38 | 2-COOMe pyridine | CF$_3$SO$_3$SiMe$_3$ | N-fluoro-2-COOMe-pyridinium $^{\ominus}$OSO$_2$CF$_3$ | 86 |

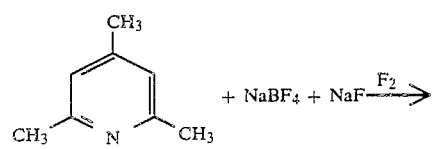

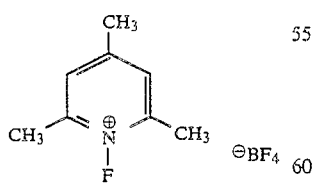

In a 25 ml pear-shaped flask, 2,4,6-trimethylpyridine (1.21 g, 10 mmoles), sodium borofluoride (1.23 g, 10 mmoles) as the XM reactant and anhydrous sodium fluoride (2.1 g, 50 mmoles) were dissolved in 15 ml of anhydrous acetonitrile and to the resulting solution a mixed gas of nitrogen/fluorine (9:1) was introduced at a rate of 50 ml/min. at −40° C. under vigorous stirring. The amount of fluorine introduced was 20 mmoles. After the completion of the reaction, precipitates were filtered and then the solvent was distilled off. The resultant residue was recrystallized from acetonitrile/diethyl ether to obtain 1.59 g (yield: 70%) of N-fluoro-2,4,6-trimethylpyridinium tetrafluoroborate the physical properties of which are shown in Table 6.

EXAMPLE 40

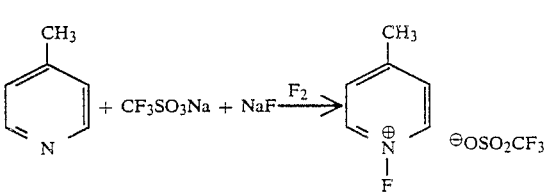

This example was effected as in example 39 to give N-fluoro-4-methylpyridinium trifluoromethanesulfonate in 90% yield, the physical properties of which are indicated in Table 6.

EXAMPLE 41-60

Further examples were carried out by using various pyridine compounds and XM. The experimental methods, the reaction products and the yields are shown in Table 4. The physical properties of the products are indicated in Table 6.

TABLE 4

| Example | Pyridine Compound | XM | Trapping Agent | Experimental Method | Product | Yield (%) |
|---|---|---|---|---|---|---|
| 41 | (1,2,3,4,5,6,7,8-octahydroacridine) | CF$_3$SO$_3$Na | — | Ex. 16 | N-F acridinium, $^\ominus$OSO$_2$CF$_3$ | 76 |
| 42 | 4-substituted pyridine (cation) | CF$_3$SO$_3$Na | NaF | Ex. 39 | N-F pyridinium, $^\ominus$OSO$_2$CF$_3$ | 86 |
| 43 | 4-substituted pyridine (cation) | NaBF$_4$ | NaF | Ex. 39 | N-F pyridinium, $^\ominus$BF$_4$ | 65 |
| 44 | 2,6-disubstituted pyridine | CF$_3$SO$_3$Na | NaF | Ex. 39 | N-F pyridinium, $^\ominus$OSO$_2$CF$_3$ | 26 |
| 45 | 4-substituted pyridine | NaClO$_4$ | — | Ex. 39 | N-F pyridinium, $^\ominus$ClO$_4$ | 81 |
| 46 | 3,5-bis(methoxycarbonyl)pyridine | CF$_3$SO$_3$SiMe$_3$ | — | Ex. 27 | N-F 3,5-bis(methoxycarbonyl)pyridinium, $^\ominus$OSO$_2$CF$_3$ | 60 |
| 47 | 4-methoxypyridine | CF$_3$SO$_3$Na | NaF | Ex. 39 | N-F 4-methoxypyridinium, $^\ominus$OSO$_2$CF$_3$ | 87 |
| 48 | 3-methoxypyridine | CF$_3$SO$_3$Na | NaF | Ex. 39 | N-F 3-methoxypyridinium, $^\ominus$OSO$_2$CF$_3$ | 62 |

TABLE 4-continued

| Example | Pyridine Compound | XM | Trapping Agent | Experimental Method | Product | Yield (%) |
|---|---|---|---|---|---|---|
| 49 | 2-acetylpyridine | CF$_3$SO$_3$Na | — | Ex. 16 | N-fluoro-2-acetylpyridinium triflate | 72 |
| 50 | 2,3,5,6-tetramethylpyridine | CF$_3$SO$_3$Na | NaF | Ex. 39 | N-fluoro-2,3,5,6-tetramethylpyridinium triflate | 33 |
| 51 | 2,3,4,5,6-pentamethylpyridine | CF$_3$SO$_3$SiMe$_3$ | NaF | Ex. 39 | N-fluoro-2,3,4,5,6-pentamethylpyridinium triflate | 18 |
| 52 | 2,6-diphenylpyridine | CF$_3$SO$_3$SiMe$_3$ | — | Ex. 2 | N-fluoro-2,6-diphenylpyridinium triflate | 15 |
| 53 | 2,4,6-tri-tert-pyridine | CF$_3$SO$_3$Na | NaF | Ex. 39 | N-fluoro product | 1.3 |
| 54 | 2-fluoromethyl-4,6-dimethylpyridine | CF$_3$SO$_3$SiMe$_3$ | — | Ex. 1 | N-fluoro-2-fluoromethyl-4,6-dimethylpyridinium triflate | little |
| 55 | 2,6-bis(fluoromethyl)-4-methylpyridine | CF$_3$SO$_3$SiMe$_3$ | — | Ex. 1 | N-fluoro-2,6-bis(fluoromethyl)-4-methylpyridinium triflate | little |
| 56 | 3,5-bis(trifluoromethyl)pyridine | CF$_3$SO$_3$SiMe$_3$ | — | Ex. 27 | N-fluoro-3,5-bis(trifluoromethyl)pyridinium triflate | 68 |
| 57 | 2-(benzoyloxymethyl)pyridine | CF$_3$SO$_3$Na | NaF | Ex. 39 | N-fluoro-2-(benzoyloxymethyl)pyridinium triflate | 84 |

TABLE 4-continued

| Example | Pyridine Compound | XM | Trapping Agent | Experimental Method | Product | Yield (%) |
|---|---|---|---|---|---|---|
| 58 | 3-methylpyridine | CF₃SO₃Na | NaF | Ex. 39 | N-fluoro-3-methylpyridinium triflate | 56 |
| 59* | 2,6-disubstituted-4-methylpyridine | CF₃SO₃Na | Na₂CO₃ | Ex. 39 | N-fluoro-2,6-disubstituted-4-methylpyridinium triflate | 10 |
| 60 | 2-difluoromethyl-4,6-dimethylpyridine | CF₃SO₃SiMe₃ | — | Ex. 1 | N-fluoro-2-difluoromethyl-4,6-dimethylpyridinium triflate | little |

*Acetonitril - water (1:1) is used as a reaction medium.

EXAMPLE 61

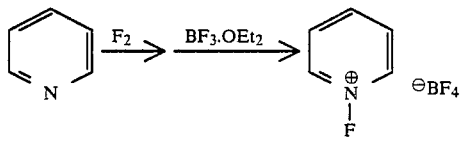

To a 30 ml anhydrous acetonitrile solution containing 0.71 g (8.98 mmole) of pyridine a mixed gas of fluorine and nitrogen (1:9) was introduced at a rate of 20 ml/min. at −40° C. under vigorous stirring, the amount of fluorine gas introduced being 26 mmoles. Subsequently, at the same temperature, 1 ml (8.13 mmole) of an ethereal complex of boron trifluoride as the Lewis acid was added and the resulting solution was stirred for 5 hours. The post treatment was effected as in example 13 to give 0.91 g (yield: 69%) of N-fluoropyridinium tetrafluoroborate, the physical properties of which are reproduced in Table 6.

EXAMPLES 62-64

These Examples 62 to 64 were carried out as in Example 61, and the results of which are summarized in Table 5 with the physical properties in Table 6. It should be noted that the appropriate amount of boron fluoride, BF₃, was introduced in the form of a gas, because BD₃ is a gas, while SbF₅ and SO₃ are introduced in liquid form.

TABLE 5

| Example No. | Pyridine-Compound | Lewis Acid | Product | Yield (%) |
|---|---|---|---|---|
| 62 | pyridine | BF₃ | N-fluoropyridinium BF₄⁻ | 62 |
| 63 | pyridine | SbF₅ | N-fluoropyridinium SbF₆⁻ | 37 |
| 64 | 2,4,6-trimethylpyridine | SO₃ | N-fluoro-2,4,6-trimethylpyridinium OSO₂F⁻ | 46 |

Example 65

TABLE 5-continued

| Example No. | Pyridine-Compound | Lewis Acid | Product | Yield (%) |
|---|---|---|---|---|
| | 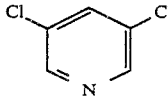 | + BF$_3$.OEt$_2$ $\xrightarrow{F_2}$ | 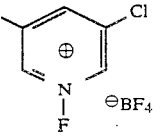 | |

This Example was carried out as in Example 16 except that boron trifluoride etherate was used in place of sodium trifluoromethanesulfonate to obtain N-fluoro-3,5-dichloropyridinum tetrafluoroborate (yield: 79%), the physical properties of which are given in Table 6.

TABLE 6

Physical Properties of N-fluoropyridinum Salts

| Example No. | Melting Point (°C.) | F-NMR (ppm) (CFCl$_3$ internal standard in CD$_3$CN) | Mass (m/e) | Elemental analysis (Calculated) C % | H % | N % |
|---|---|---|---|---|---|---|
| 1, 2, 7, 8, 27 | 185–187 | −48.75 (1F, bs, NF)<br>77.61 (3F, s, CF$_3$) | 227(M$^+$-HF) | 29.17<br>(29.16) | 1.99<br>(2.04) | 5.66<br>(5.67) |
| 3 | 41–42 | −46.89 (1F, bs, NF)<br>77.75 (3F, s, CF$_3$) | 255(M$^+$-H) | 34.72<br>(34.91) | 3.35<br>(3.30) | 5.07<br>(5.09) |
| 4 | 202 (decomposition) | −48.58 (1F, bs, NF)<br>71.68 (6F, d, J = 715 Hz, PF$_6$) | 174, 172<br>107, 97 | 24.84<br>(24.69) | 2.10<br>(2.06) | 5.65<br>(5.76) |
| 5, 63 | >300 | −48.82 (1F, bs, NF)<br>69.0–175.0 (6F, m, SbF$_6$) | 278, 276<br>(M$^+$−3F) | 18.02<br>(17.96) | 1.50<br>(1.50) | 4.09<br>(4.19) |
| 6 | 225–227.5 (with decompo.) | −48.75 (1F, bs, NF) | 156, 155, 97, 79 | 30.50<br>(30.38) | 2.23<br>(2.53) | 7.12<br>(7.09) |
| 9, 10, 29 | 99.5–101 | −52.13 (1F, bs, NF)<br>77.63 (3F, s, CF$_3$) | 299, 297<br>295 (M$^+$-HF) | 22.68<br>(22.80) | 0.94<br>(0.96) | 4.58<br>(4.43) |
| 11 | 120–125 | −48.18 (1F, bs, NF)<br>−38.21 (1F, s, S) | 177 (M$^+$-HF)<br>149 | 30.56<br>(30.46) | 2.57<br>(2.56) | 7.03<br>(7.10) |
| 12 | 135–136.5 | −17.25 (bs, NF) | 151, 139 | 58.00<br>(58.20) | 7.05<br>(7.05) | 3.74<br>(3.77) |
| 13, 64 | 162–164 (decomposition) | −38.21 (1F, s, SO$_2$F)<br>−17.25 (1F, bs, NF) | 237<br>219(M$^+$-HF) | 39.36<br>(40.16) | 4.52<br>(4.60) | 5.90<br>(5.89) |
| 14 | 24–25.5 | −17.63 (1F, bs, NF)<br>75.00 (3F, s, CF$_3$) | — | — | — | — |
| 15, 17 | 168.5–170 | −17.25 (1F, bs, NF)<br>77.62 (3F, s, CF$_3$) | 139<br>121 | 37.15<br>(37.37) | 3.87<br>(3.84) | 4.66<br>(4.84) |
| 16 | 126–128 | −24.75 (1F, bs, NF)<br>77.75 (3F, s, CF$_3$) | 255(M$^+$-HF) | 34.86<br>(34.91) | 3.26<br>(3.30) | 5.03<br>(5.09) |
| 18, 25, 34 | 140–143 | −25.50 (1F, bs, NF)<br>77.61 (3F, s, CF$_3$) | 227, 137, 69, 59 | 30.31<br>(30.32) | 2.52<br>(2.53) | 5.07<br>(5.05) |
| 19 | 111–112 | −48.37 (1F, bs, NF),<br>80.30 (3F,tt,J = 10.1,3.0Hz,CF$_3$)<br>114.2 (2F,m,CF$_2$),120.9(2F,m,CF$_2$),<br>125.2 (2F,M,CF$_2$S) | 377(M$^+$-HF) | 27.08<br>(27.22) | 1.35<br>(1.27) | 3.55<br>(3.53) |
| 20 | 119.5–120.5 | −37.13 (1F, bs, NF)<br>77.25 (3F, s, CF$_3$) | — | — | — | — |
| 21 | 95–96 | −0.75 (1F, bs, NF)<br>77.58 (3F, s, CF$_3$) | 182, 179, 128<br>113, 95, 69 | 30.31<br>(30.32) | 2.52<br>(2.53) | 5.07<br>(5.05) |
| 22 | 111–111.5 (decomposition) | −0.75 (1F, bs, NF)<br>77.62 (3F, s, CF$_3$) | — | 47.70<br>(47.87) | 5.87<br>(5.77) | 3.46<br>(3.49) |
| 23 | 111.5–112.5 | −51.00 (1F, bs, NF)<br>77.61 (3F, s, CF$_3$) | 243, 187, 186<br>137, 135, 113 | 31.72<br>(31.48) | 2.02<br>(2.30) | 4.43<br>(4.60) |
| 24 | 88–91 | −39,38 (1F, bs, NF)<br>77.63 (3F, s, CF$_3$) | — | — | — | — |
| 26 | 79–80 | −25.05 (1F, bs, NF)<br>77.98 (3F, s, CF$_3$) | 163<br>137 | — | — | — |
| 28 | 55–58 | −48.75 (1F, bs, NF) (*) | 173 (M$^+$-HF) | — | — | — |
| 30 | 108–109 | −50.59 (1F, bs, NF)<br>70.70 (3F, s, CF$_3$) | 263, 261<br>(M$^+$-HF) | 26.38<br>(26.52) | 1.53<br>(1.47) | 5.81<br>(5.17) |
| 31, 33 | 105–108 | −54.22 (1F, bs, NF)<br>61.50 (3F, s, CF$_3$)<br>78.10 (3F, s, CF$_3$S) | 341, 199<br>197 | 23.81<br>(24.05) | 1.12<br>(0.86) | 3.98<br>(4.01) |
| 32 | 115–116 | −50.02 (1F, bs, NF)<br>77.68 (3F, s, CF$_3$) | 299 (M$^+$-HF) | 33.74<br>(33.86) | 2.73<br>(2.85) | 4.28<br>(4.39) |
| 35 | 57–65 | −53.25 (1F, bs, NF)<br>77.61 (3F, s, CF$_3$) | — | — | — | — |
| 36 | 110–115 (decomposition) | −36.38 (1F, bs, NF)<br>77.61 (3F, s, CF$_3$) | — | — | — | — |
| 37 | 112–116 | −54.75 (1F, bs, NF)<br>77.61 (3F, s, CF$_3$) | — | — | — | — |
| 38 | 115–116 | −38.44 (1F, bs, NF)<br>78.04 (3F, s, CF$_3$) | 137, 107, 79, 78 | 31.49<br>(31.48) | 2.28<br>(2.30) | 4.59<br>(4.59) |
| 39 | 215–217 | −17.25 (1F, bs, NF)<br>149.6 (4F, s, BF$_4$) | 157, 139 | 42.37<br>(42.33) | 4.75<br>(4.88) | 6.24<br>(6.17) |

TABLE 6-continued
Physical Properties of N-fluoropyridinum Salts

| Example No. | Melting Point (°C.) | F-NMR (ppm) (CFCl₃ internal standard in CD₃CN) | Mass (m/e) | C % | H % | N % |
|---|---|---|---|---|---|---|
| 40 | 84–88 | −40.50 (1F, bs, NF)<br>77.48 (3F, s, CF₃) | 241 (M⁺-HF) | 32.12<br>(32.19) | 2.87<br>(2.70) | 5.25<br>(5.36) |
| 41 | 149.5–152 | −19.75 (1F, bs, NF)<br>78.00 (3F, s, CF₃) | — | — | — | — |
| 42 | 116–118 | −40.05 (1F, bs, NF)<br>78.02 (3F, s, CF₃) | 268 (M⁺-HF)<br>135, 120 | 39.29<br>(39.60) | 4.22<br>(4.32) | 4.50<br>(4.62) |
| 43 | 143–145 | −39.99 (1F, bs, NF)<br>150.6 (4F, s, BF₄) | 138, 110 | 44.21<br>(44.85) | 5.32<br>(5.44) | 5.64<br>(5.81) |
| 44 | 112–114 | −23.63 (1F, bs, NF)<br>78.00 (3F, s, CF₃) | 210, 190 | 46.56<br>(46.80) | 5.89<br>(5.85) | 3.86<br>(3.90) |
| 45 | 146–148 | −40.00 (bs, NF) | 120 | — | — | — |
| 46 | 144–147 | −51.88 (1F, bs, NF)<br>78.00 (3F, s, CF₃) | 343 (M⁺-HF),<br>248, 182 | 32.84<br>(33.07) | 2.46<br>(2.50) | 3.84<br>(3.86) |
| 47 | 32 | −27.38 (1F, bs, NF)<br>77.25 (3F, s, CF₃) | 258<br>257(M⁺-HF), 69 | 30.35<br>(30.33) | 2.61<br>(2.55) | 5.02<br>(5.05) |
| 48 | viscous | −50.10 (1F, bs, NF)<br>77.20 (1F, s, CF₃) | 108 | — | — | — |
| 49 | 151–152 | −37.5 (1F, bs, NF)<br>77.30 (3F, s, CF₃) | — | — | — | — |
| 50 | 136–138 | −28.88 (1F, bs, NF)<br>78.00 (3F, s, CF₃) | 283 (M⁺-HF)<br>135 | 39.84<br>(39.60) | 4.36<br>(4.29) | 4.41<br>(4.62) |
| 51 | 97–97.5 | −27.00 (1F, bs, NF)<br>77.62 (3F, s, CF₃) | 168, 167<br>149 | 51.83<br>(52.05) | 6.95<br>(6.99) | 3.33<br>(3.37) |
| 52 | 131–133 | −19.50 (1F, bs, NF)<br>77.25 (3F, s, CF₃) | 249<br>231 | 53.72<br>(54.10) | 3.19<br>(3.26) | 3.42<br>(3.51) |
| 53 | 238–239 | −17.25 (1F, bs, NF)<br>77.25 (3F, s, CF₃) | 266, 246<br>232, 205 | 41.20<br>(41.38) | 4.75<br>(4.70) | 4.33<br>(4.39) |
| 54 | 162.5–163.5 | −15.75 (1F, bs, NF)<br>77.72 (3F, s, CF₃)<br>226.5 (1F, dt, J = 45, 10.5Hz, CH₂F) | 139<br>121 | 35.07<br>(35.18) | 3.26<br>(3.26) | 4.43<br>(4.56) |
| 55 | 160–163 | −14.63 (1F, bs, NF)<br>77.62 (3F, bs, CF₃)<br>228.0 (2F, dt, J = 45, 10.2Hz, CH₂F) | 306, 305<br>157 | 32.65<br>(33.23) | 2.70<br>(2.77) | 4.14<br>(4.31) |
| 56 | 193–195 | −54.75 (1F, bs, NF)<br>61.50 (6F, s, β-CF₃)<br>78.00 (3F, s, CF₃) | 375<br>271<br>69 | 24.9<br>(25.08) | 0.85<br>(0.79) | 3.64<br>(3.66) |
| 57 | 94–96 | −36.37 (1F, bs, NF)<br>77.40 (3F, s, CF₃) | 361<br>(M⁺-HF) | 43.63<br>(44.10) | 2.72<br>(2.91) | 3.58<br>(3.67) |
| 58 | viscous | −46.88 (1F, bs, NF)<br>78.00 (3F, s, CF₃) | 241<br>(M⁺-HF) | 31.17<br>(32.18) | 2.72<br>(2.68) | 5.26<br>(5.36) |
| 59 | 159 | −15.75 (1F, bs, NF)<br>76.87 (3F, s, NF) | 359<br>338<br>190 | 48.04<br>(47.75) | 6.27<br>(6.14) | 3.68<br>(3.71) |
| 60 | 162–168 | −15.75 (1F, bs, NF)<br>77.68 (3F, s, CF₃)<br>119.3 (2F, dd, J = 52.5, 10.6 Hz, CHF₂) | 306, 305<br>175, 172<br>157, 156 | 33.11<br>(33.23) | 2.68<br>(2.77) | 4.20<br>(4.31) |
| 61, 62 | 90–91 | −48.75 (1F, bs, NF)<br>149.6 (4F, s, BF₄) | 104 | 32.53<br>(32.43) | 2.64<br>(2.70) | 7.43<br>(7.57) |
| 65 | 208–209 | −52,67 (1F, bs, NF)<br>150.5 (4F, s, BF₄) | 169<br>167 (M⁺-HBF₄)<br>165 | 23.62<br>23.62 | 1.11<br>1.11 | 5.44<br>5.44 |

The Following Examples 66–133 are contemplated to elucidate the use of the compounds according to the present invention as the fluorine introducing agent.

EXAMPLE 66

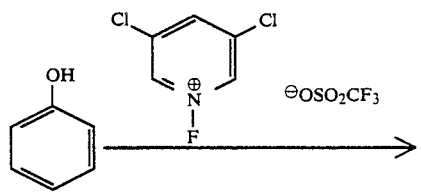

⟶

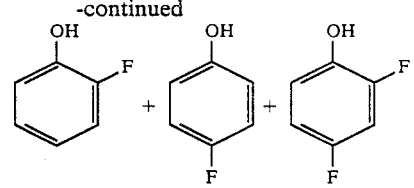

A methylene chloride solution (1 ml) containing 1.0 mmole of phenol and 1.0 mmole of N-fluoro-3,5-dichloropyridinium trifluoromethanesulfonate was refluxed under an argon atmosphere for 5 hours. After the reaction was completed, the reaction solution was analysed by gas chromatography to reveal that it contained o-fluorophenol (0.44 mmole), p-fluorophenol (0.13 mmole), 2,4-difluorophenol (0.06 mmole), and phenol (0.27 mmole). Thus the yields of o-fluorophenol, p-fluorophenol and 2,4-difluorophenol were 60%, 18%, and 7% respectively. The total yield was 85% corresponding to the total conversion of 73%. It is noted that no m-fluorophenol was formed.

EXAMPLE 67

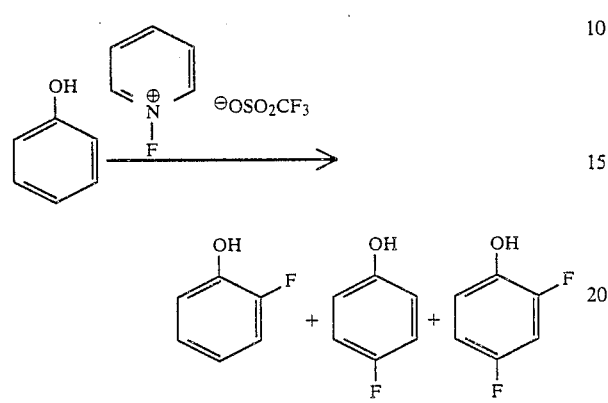

A 1,1,2-trichloroethane solution (2 ml) containing 1.0 mmole of phenol and 0.5 mmole of N-fluoropyridinium trifluoromethanesulfonate was heated at 100° C. for 24 hours under an argon atmosphere and 0.25 mmole of additional N-fluoropyridinium trifluoromethanesulfonate, was added both after 3 hours and 6 hours, thus bringing the total amount of N-fluoropyridinium trifluoromethanesulfonate to 1.0 mmole. After the reaction, the resulting reaction solution was subjected to gas chromatography to reveal that it contained 0.40 mmole of o-fluorophenol, 0.14 mmole of p-fluorophenol, 0.05 mmole of 2,4-difluorophenol and 0.21 mmole of phenol. Therefore, the yields of o-, p-fluorophenols and 2,4-difluoro-phenol were 51%, 18% and 6% respectively, corresponding to the total yields to 75%, with the total conversion of 79%.

EXAMPLES 68-133

A wide variety of fluorine- containing compounds were prepared by reacting N-fluoropyridinium salts according to the present invention with an equi-molar amount of compounds contemplated to be fluorinated. These examples were carried out similar to Example 66 with the reaction conditions set forth in Tables 7-10. The results obtained are also indicated in Tables 7-10. The identification of the structures of the resulting compounds were effected by comparing those with a standard specimen or with spectroscopy.

In Tables 7-10, the N-fluoropydinium salts set foth below were expressed, for simplicity' sake, with the following No. of compounds:

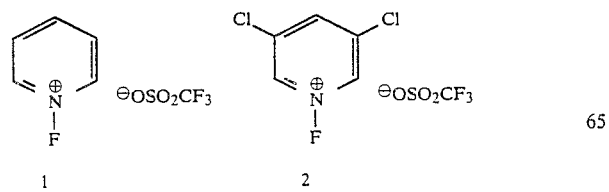

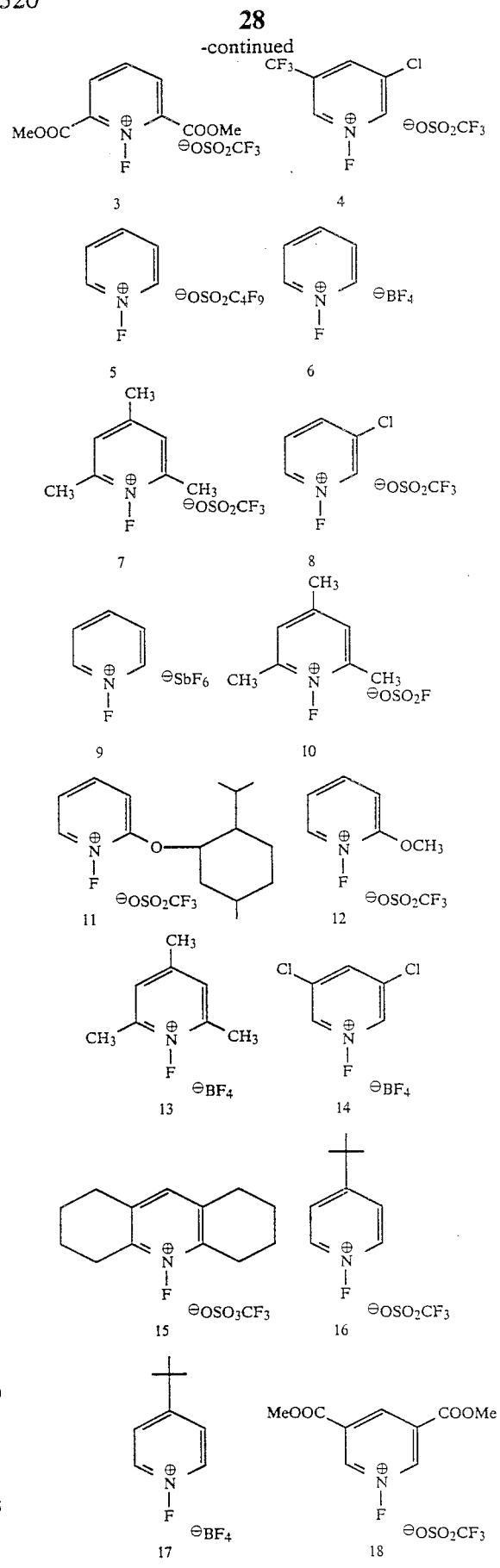

TABLE 7

| Example No. | Aromatic Compound | N-Fluoropyridinium salt (indicated by compound number) | Solvent | Temperature (°C.) | Hours (h) | Conversion (%) | Fluorine containing compound | Yield (%) | 19F-NMR (ppm) (CFCl3 internal standard in CDCl3) |
|---|---|---|---|---|---|---|---|---|---|
| 68 | phenol | 3 | CH2Cl2 | room temp. | 18 | 78 | o-fluorophenol | 30 | — |
|  |  |  |  |  |  |  | p-fluorophenol | 24 | — |
|  |  |  |  |  |  |  | 2,4-difluorophenol | 3 | — |
| 69 | phenol | 4 | CH2Cl2 | reflux temp. | 5 | — | o-fluorophenol | 40 | — |
|  |  |  |  |  |  |  | p-fluorophenol | 11 | — |
|  |  |  |  |  |  |  | 2,4-difluorophenol | 5 | — |
| 70 | phenol | 5 | CH2ClCHCl2 | 100 | 16 | 80 | o-fluorophenol | 49 | — |
|  |  |  |  |  |  |  | p-fluorophenol | 14 | — |
|  |  |  |  |  |  |  | 2,4-difluorophenol | trace | — |
| 71 | phenol | 6 | CH2ClCHCl2 | reflux temp. | 72 | 73 | o-fluorophenol | 24 | — |
| 72 | phenol | 7 | CH2ClCHCl2 | 100 | 24 | 75 | o-fluorophenol | 47 | — |
|  |  |  |  |  |  |  | p-fluorophenol | 31 | — |
|  |  |  |  |  |  |  | 2,4-difluorophenol | 3 | — |
| 73 | phenol | 14 | CH2Cl2 | reflux temp. | 24 | 63 | o-fluorophenol | 84 | — |
|  |  |  |  |  |  |  | p-fluorophenol | 10 | — |
|  |  |  |  |  |  |  | 2,4-difluorophenol | 1 | — |
| 74 | phenol | 16 | CH2ClCHCl2 | 120 | 10 | 70 | o-fluorophenol | 45 | — |
|  |  |  |  |  |  |  | p-fluorophenol | 15 | — |
| 75 | phenol | 17 | CH2ClCHCl2 | 120 | 10 | 70 | o-fluorophenol | 42 | — |
|  |  |  |  |  |  |  | p-fluorophenol | 15 | — |
| 76 | anisole | 2 | CH2ClCH2Cl | reflux temp. | 18 | 65 | o-fluoroanisole | 48 | — |
|  |  |  |  |  |  |  | p-fluoroanisole | 51 | — |
| 77 | anisole | 1 | CH2ClCH2Cl | reflux temp. | 18 | 58 | o-fluoroanisole | 40 | — |
|  |  |  |  |  |  |  | p-fluoroanisole | 47 | — |
| 78 | anisole | 3 | CH2Cl2 | reflux temp. | 24 | 71 | o-fluoroanisole | 44 | — |
|  |  |  |  |  |  |  | p-fluoroanisole | 48 | — |
| 79 | ![HO-C6H4-CH2COOCH3] | 2 | CH2Cl2 | reflux temp. | 5 | 57 | ![F, HO-C6H3-CH2COOCH3] | 71 | 140.3 |
| 80 | ![HO-C6H4-CH2COOCH3] | 3 | CH2Cl2 | reflux temp. | 3 | 79 | ![F, HO-C6H3-CH2COOCH3] | 46 | 140.3 |
|  |  |  |  |  |  |  | ![F, O=C6H4-CH2COOCH3 (cyclohexadienone)] | 23 | 149.6 |

TABLE 7-continued

| Example No. | Aromatic Compound | N-Fluoropyridinium salt (indicated by compound number) | Solvent | Temperature (°C.) | Hours (h) | Conversion (%) | Fluorine containing compound | Yield (%) | $^{19}$F-NMR (ppm) (CFCl$_3$ internal standard in CDCl$_3$) |
|---|---|---|---|---|---|---|---|---|---|
| 81 | 4-HO-C$_6$H$_4$-CH$_2$COOMe | 18 | CH$_2$Cl$_2$ | reflux temp. | 50 | 85 | 3-F-4-HO-C$_6$H$_3$-CH$_2$COOMe | 55 | 140.3 |
| 82 | 4-HO-C$_6$H$_4$-CH$_2$COOCH$_3$ | 2 | CH$_2$Cl$_2$ | reflux temp. | 47 | 78 | 3-F-4-HO-C$_6$H$_3$-CH$_2$COOCH$_3$ | 51 | 140.3 |
| 83 | 4-CH$_3$O-C$_6$H$_4$-CH$_2$COOCH$_3$ | 3 | CH$_2$Cl$_2$ | reflux temp. | 25 | 62 | 3-F-4-CH$_3$O-C$_6$H$_3$-CH$_2$COOCH$_3$ | 47 | 134.6 |
| | | | | | | | 4-F-4-(CH$_2$COOCH$_3$)-cyclohexa-2,5-dienone | 31 | 149.6 |
| 84 | C$_6$H$_5$-NHCOCH$_3$ | 3 | CH$_2$Cl$_2$ | reflux temp. | 48 | 53 | 2-F-C$_6$H$_4$-NHCOCH$_3$ | 28 | 130.5 |
| | | | | | | | 4-F-C$_6$H$_4$-NHCOCH$_3$ | 24 | 117.8 |
| 85 | C$_6$H$_5$-NHCOOEt | 3 | CH$_2$Cl$_2$ | reflux temp. | 32 | 68 | 2-F-C$_6$H$_4$-NHCOOEt | 47 | 131.9 |
| | | | | | | | 4-F-C$_6$H$_4$-NHCOOEt | 32 | 119.1 |

TABLE 7-continued

| Example No. | Aromatic Compound | N-Fluoropyridinium salt (indicated by compound number) | Solvent | Temperature (°C.) | Hours (h) | Conversion (%) | Fluorine containing compound | Yield (%) | 19F-NMR (ppm) (CFCl3 internal standard in CDCl3 |
|---|---|---|---|---|---|---|---|---|---|
| 86 | 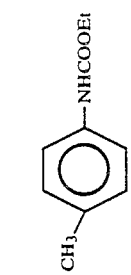 p-t-butylphenol | 2 | CH2Cl2 | reflux temp. | 38 | 56 | 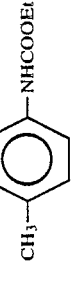 | 5<br>71 | 115.8<br>126.7<br>133.1 |
| 87 | p-t-butylphenol | 2 | CH2Cl2 | reflux temp. | 27 | 83 | 2-fluoro-4-t-butylphenol<br>p-fluorophenol | 68<br>7 | 139.1<br>123.5 |
| 88 | 2-naphthol | 2 | CH2Cl2 | room temp. | 26 | 80 | 1-fluoro-2-naphthol | 84<br>11 | 155.2<br>101.6 |
| 89 | benzene | 3 | benzene | reflux temp. | 24 | — | fluorobenzene | 56 | 111.4<br>(in benzene solvent) |

TABLE 8

| Example No. | Enol Compound | N-Fluoropyridinum salt (indicated by compound number) | Solvent | Temperature (°C.) | Hours (h) | Fluorine Containing compound | Yield (%) | ¹⁹F-NMR (ppm) (CFCl₃ internal standard in CDCl₃) |
|---|---|---|---|---|---|---|---|---|
| 90 | cyclohexenyl-OSiMe₃ | 1 | CH₂Cl₂ | room temp. | 7 | 2-fluorocyclohexanone | 87 | 188 (d, J=50Hz) |
| 91 | cyclohexenyl-OSiMe₃ | 7 | CH₂Cl₂ | room temp. | 4 | 2-fluorocyclohexanone | 57 | 188 (d, J=50Hz) |
| 92 | cyclohexenyl-OSiMe₃ | 8 | CH₂Cl₂ | room temp. | 3 | 2-fluorocyclohexanone | 65 | 188 (d, J=50Hz) |
| 93 | cyclohexenyl-OSiMe₃ | 2 | CH₂Cl₂ | room temp. | 2 | 2-fluorocyclohexanone | 62 | 188 (d, J=50Hz) |
| 94 | cyclohexenyl-OSiMe₃ | 6 | CH₂Cl₂ | reflux temp. | 6 | 2-fluorocyclohexanone | 41 | 188 (d, J=50Hz) |
| 95 | cyclohexenyl-OSiMe₃ | 9 | CH₂Cl₂ | reflux temp. | 8 | 2-fluorocyclohexanone | 23 | 188 (d, J=50Hz) |
| 96 | cyclohexenyl-OSiMe₃ | 5 | CH₂Cl₂ | room temp. | 5 | 2-fluorocyclohexanone | 69 | 188 (d, J=50Hz) |

TABLE 8-continued

| Example No. | Enol Compound | N-Fluoropyridinium salt (indicated by compound number) | Solvent | Temperature (°C.) | Hours (h) | Fluorine Containing compound | Yield (%) | $^{19}$F-NMR (ppm) (CFCl$_3$ internal standard in CDCl$_3$) |
|---|---|---|---|---|---|---|---|---|
| 97 | cyclohexenyl-OSiMe$_3$ | 10 | CH$_2$Cl$_2$ | reflux temp. | 24 | 2-fluorocyclohexanone | 40 | 188 (d,J=50Hz) |
| 98 | cyclohexenyl-OAc | 3 | CH$_2$Cl$_2$ | reflux temp. | 3 | 2-fluorocyclohexanone | 24 | 188 (d,J=50Hz) |
| 99 | PhCH=C(OEt)(OSiMe$_3$) | 1 | CH$_2$Cl$_2$ | room temp. | 2 | PhCHFCOOEt | 65 | 180 (d,J=48Hz) |
| 100 | PhCH=C(OEt)(SOiMe$_3$) | 7 | CH$_2$Cl$_2$ | room temp. | 2 | PhCHFCOOEt | 71 | 180 (d,J=48Hz) |
| 101 | PhCH=C(OSiMe$_3$)(OSiMe$_3$) | 7 | CH$_2$Cl$_2$ | room temp. | 2 | PhCHFCOOH | 68 | 181 (d,J=48Hz) |
| 102 | PhCH=C(OSiMe$_3$)(OSiMe$_3$) | 11 | CH$_2$Cl$_2$ | room temp. | 2 | PhCHFCOOH | 70 | 181 (d,J=48Hz) |
| 103 | n-C$_7$H$_{14}$—CH=C(OSiMe$_3$)—CH$_3$ | 1 | CH$_2$Cl$_2$ | reflux temp. | 3 | n-C$_7$H$_{14}$—CHF—CO—CHCH$_3$ (with F) | 58 | 188(m) |
| 104 | octahydronaphthalenyl-OSiMe$_3$ | 1 | CH$_2$Cl$_2$ | room temp. | 3 | fluorinated octalone | 31 | 168 (t,J=51Hz) |

TABLE 8-continued

| Example No. | Enol Compound | N-Fluoropyridinum salt (indicated by compound number) | Solvent | Temperature (°C.) | Hours (h) | Fluorine Containing compound | Yield (%) | 19F-NMR (ppm) (CFCl3 internal standard in CDCl3) |
|---|---|---|---|---|---|---|---|---|
| 105 | [steroid enol with OSiMe3 and Me3SiO groups] | 1 | CH2Cl2 | room temp. | 1 | [decalone with F] | 21 | 184 (d,J=50Hz) |
| | | | | | | [decalone with F adjacent to C=O] | 10 | 206 (d,J=50Hz) |
| | | | | | | [steroid with OH and F] | 31 | 166 (t,J=50Hz) |
| | | | | | | [steroid with OH and F] | 11 | 183 (d,J=50Hz) |
| | | | | | | [steroid with OH and F] | 18 | 206 (d,J=50Hz) |

TABLE 8-continued

| Example No. | Enol Compound | N-Fluoropyridinium salt (indicated by compound number) | Solvent | Temperature (°C.) | Hours (h) | Fluorine Containing compound | Yield (%) | $^{19}$F-NMR (ppm) (CFCl$_3$ internal standard in CDCl$_3$) |
|---|---|---|---|---|---|---|---|---|
| 106 | [steroid with OAc, AcO] | 1 | CH$_2$Cl$_2$ | reflux temp. | 10 | [fluorinated steroid with OAc] | 48 | 166 (t, J=48Hz) |
|  |  |  |  |  |  | [fluorinated steroid with OAc] | 24 | 184 (d, J=48Hz) |
| 107 | [steroid with OAc, AcO] | 1 | CH$_2$Cl$_2$ | reflux temp. | 14 | [fluorinated steroid with OAc] | 31 | 166 (t, J=49.5Hz) |
|  |  |  |  |  |  | [fluorinated steroid with OAc] | 20 | 183 (d, J=50Hz) |

TABLE 8-continued

| Example No. | Enol Compound | N-Fluoropyridinum salt (indicated by compound number) | Solvent | Temperature (°C.) | Hours (h) | Fluorine Containing compound | Yield (%) | $^{19}$F-NMR (ppm) (CFCl$_3$ internal standard in CDCl$_3$) |
|---|---|---|---|---|---|---|---|---|
| 108 | steroid enol with OSiMe$_3$ and AcO groups | 1 | CH$_2$Cl$_2$ | reflux temp. | 2 | fluorinated steroid with F and AcO groups | 59 | 192(m) |
| 109* | steroid enol with OH and morpholine-N group | 15 | CH$_2$Cl$_2$—CH$_3$CN (4/1) | −15 | 1 | fluorinated steroid with OH, F, and ketone | 63 | 138(s) |
| 110 | cyclopentene with OH and COOEt | 2 | CH$_2$Cl$_2$ | reflux temp. | 24 | fluorinated cyclopentanone with F and COOEt | 72 | 163 (t, J=20Hz) |
| 111 | cyclopentene with OH and COOEt | 7 | CH$_2$Cl$_2$ | reflux temp. | 48 | fluorinated cyclopentanone with F and COOEt | 83 | 163 (t, J=20Hz) |
| 112 | cyclopentene with OH and COOEt | 12 | CH$_2$Cl$_2$ | reflux temp. | 48 | fluorinated cyclopentanone with F and COOEt | 68 | 163 (t, J=20Hz) |
| 113 | cyclopentenedione with OH | 2 | CH$_2$Cl$_2$ | reflux temp. | 15 | fluorinated methyl cyclopentanedione | 48 | 171 (q, J=28Hz) |

TABLE 8-continued

| Example No. | Enol Compound | N-Fluoropyridinium salt (indicated by compound number) | Solvent | Temperature (°C.) | Hours (h) | Fluorine Containing compound | Yield (%) | ¹⁹F-NMR (ppm) (CFCl₃ internal standard in CDCl₃) |
|---|---|---|---|---|---|---|---|---|
| 114 | OCH₃ (cyclohexene) | 1 | CH₂Cl₂ | reflux temp. | 0.4 | OCH₃, F (cyclohexene) | 59 | 177(m) |

*the reaction product was hydrorized in a DMF-conc. Hcl aqueous soln. (8:1).

TABLE 9

| Example No. | Carbon anion | H-Fluoropyridnum salt (indicated by compound number) | Solvent | Temperature (°C.) | Hours (h) | Fluorine containing compound | Yield (%) | $^{19}$F-NMR (ppm) (CFCl$_3$ internal standard in CDCl$_3$) |
|---|---|---|---|---|---|---|---|---|
| 115 | cyclopentanone-2-COOEt anion | 7 | THF | room temp. | 0.17 | 2-F-2-COOEt-cyclopentanone | 78 | 162.8 (t, J=20.3Hz) |
| 116 | Na⊕, 1,3-cyclopentanedione-2-anion | 7 | THF | room temp. | 1 | 2-F-1,3-cyclopentanedione | 44 | 172.5 (q, J=22.5Hz) |
| 117 | Na⊕, ⊖CH(COOEt)$_2$ | 7 | THF | 0 | 0.17 | FCH(COOEt)$_2$ | 78 | 158.0 (q, J=21.9Hz) |
| 118 | Na⊕, ⊖CH(COOEt)$_2$ | 7 | THF | 0 | 2 | FCH(COOEt)$_2$ | 42 | 144.6 (q, J=48.6Hz) |
|  |  |  |  |  |  | F$_2$C(COOEt)$_2$ | 6 | 111.0(s) |
| 119 | Na⊕, Ph−⊖C(CN)$_2$ | 7 | THF | 0 → room temp. | 0.17 | Ph−CF(CN)$_2$ | 71 | 118.9(s) |
| 120 | n-C$_{12}$H$_{25}$MgCl | 7 | Et$_2$O | 0 | 0.5 | n-C$_{12}$H$_{25}$F | 75 | 210.8 (tt, J=51.3, 17Hz) |
| 121 | PhMgCl | 7 | THF | 0 | 0.17 | PhF | 58 | — |
| 122 | Na⊕, PhSO$_2$⊖CHCOOMe | 7 | THF | 0 | 1 | PhSO$_2$CHFCOOMe | 50 | 179.6 (d, J=49.6Hz) |

TABLE 10

| Example No. | Sulfide | H-Fluoropyridinum salt (indicated by compound number) | Solvent | Temperature (°C.) | Hours (h) | α-fluorosulfide | Yield (%) | Solvent | F-NMR (ppm) (CFCl₃ internal standard) SCF (ppm) |
|---|---|---|---|---|---|---|---|---|---|
| 123 | 4-Cl-C₆H₄-SCH₃ | 7 | $CH_2Cl_2$ | room temp. | 8 | 4-Cl-C₆H₄-SCH₂F | 87 | $CDCl_3$ | 182.8 (t, 52.5Hz) |
| 124 | 4-Cl-C₆H₄-SCH₃ | 1 | $CH_2Cl_2$ | room temp. | 7.5 | 4-Cl-C₆H₄-SCH₂F | 48 | $CDCl_3$ | 182.8 (t, 52.5Hz) |
| 125 | PhSCH₃ | 7 | $CH_2Cl_2$ | room temp. | 4 | PhSCH₂F | 85 | $CDCl_3$ | 180.3 (t, 54Hz) |
| 126 | PhSCH₃ | 1 | $CH_2Cl_2$ | room temp. | 6 | PhSCH₂F | 56 | $CDCl_3$ | 180.3 (t, 54Hz) |
| 127 | PhCH₂SCH₃ | 7 | $CH_2Cl_2$ | room temp. | 1 | PhCHFSCH₃   4 : PhCH₂SCH₂F  3 | 76 | $CH_2Cl_2$ $CH_2Cl_2$ | 152.0 (d, 56Hz) 187.2 (t, 51Hz) |
| 128 | PhCH₂SCH₃ | 7 | $CH_2Cl_2$ | 0 | 3 | PhCHFSCH₃   4 : PhCH₂SCH₂F  3 | 48 | $CH_2Cl_2$ $CH_2Cl_2$ | 152.0 (d, 56Hz) 187.2 (t, 51Hz) |
| 129 | n-C₁₂H₂₅SCH₃ | 7 | $CH_2Cl_2$ | room temp. | 17.5 | n-C₁₂H₂₅SCH₂F | 44 | $CH_2Cl_2$ | 184.2 (t, 52Hz) |
| 130 | CH₃SCH₂COOEt | 7 | $CH_2Cl_2$ | room temp. | 10 | CH₃SCHFCOOEt | 48 | $CH_2Cl_2$ | 167.3 (d, 54Hz) |
| 131 | CH₃SCH₂CH₂CH(NHCOCF₃)COOMe | 7 | $CH_2Cl_2$ | room temp. | 7.5 | FCH₂SCH₂CH₂CH(NHCOCF₃)COOMe | 40 | $CDCl_3$ | 183.8 (t, 51Hz) |

TABLE 10-continued

| Example No. | Sulfide | H-Fluoropyridinum salt(indicated by compound number) | Solvent | Temperature (°C.) | Hours (h) | α-fluorosulfide | Yield (%) | F-NMR (ppm) (CFCl₃ internal standard) Solvent | SCF (ppm) |
|---|---|---|---|---|---|---|---|---|---|
| 132 | 4-Cl-C₆H₄-SCH₃ | 13 | CH₂Cl₂ | 40 | 4.5 | 4-Cl-C₆H₄-SCH₂F | 75 | CDCl₃ | 182.8 (t,52.5Hz) |
| 133 | PhSC₂COOMe | 7 | CH₂Cl₂ | room temp. | 23 | PhSCHFCOOMe | 45 | CDCl₃ | 158.4 (d,52Hz) |

What is claimed is:

1. A N-fluoropyridinium salt having the general formula:

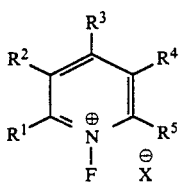

wherein:
(a) $R^1$ through $R^5$ are each a group selected from the class consisting of hydrogen, halogen, and methyl;
(b) when at least two of each of $R^1$ through $R^5$ are hydrogen, then the remaining one through three groups of $R^1$ through $R^5$ can each be selected from the class consisting of:
phenylcarbonyloxy substituted methyl,
a mixture of at least one fluoro substituted methyl group and at least one group selected from the class consisting of methyl, trifluoromethyl and halogen, and
tertiary butyl or a mixture of methyl and t-butyl provided that, when at least two of each of $R^1$ through $R^5$ are tertiary butyl, said tertiary butyl groups are not adjacent;
(c) when at least three of each of $R^1$ through $R^5$ are hydrogen, then the remaining one or two groups of $R^1$ through $R^5$ can each be selected from the class consisting of:
phenyl,
acetyl,
alkoxycarbonyl containing a total of 2 through 5 carbon atoms wherein said alkyl substituent contains a total of 1 through 4 carbon atoms,
nitro,
cyano,
alkoxy containing 1 through 10 carbon atoms, and acyloxy wherein said acyl group contains 1 through 4 carbon atoms;
(d) when $R^3$ is hydrogen, then $R^1$ and $R^2$ taken together and $R^4$ and $R^5$ taken together can each form a six-membered carbocyclic ring which is inclusive of two adjacent carbon atoms of the pyridine ring; and
(e) when $R^3$ through $R^5$ are each hydrogen, then $R^1$ and $R^2$ taken together can form a five-membered heterocyclic ring which contains one oxygen atom, which is inclusive of two carbon atoms of the pyridine ring, and which has an oxo oxygen atom substituted on each ring carbon atom adjacent said ring oxy oxygen atom; and
(f) X is a conjugate base of a Brønsted acid except for halides.

2. The N-fluoropyridinium salt of claim 1 wherein X is selected from the class consisting of:

$-OSO_2CF_3$, $-PF_6$, $-SbF_6$, $-ClO_4$, $-OSO_2F$, $-OSO_2CH_3$,

-continued

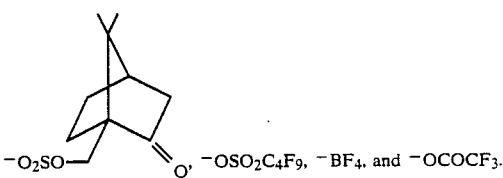

$-OSO_2C_4F_9$, $-BF_4$, and $-OCOCF_3$.

3. A process for making an N-fluoropyridinium salt comprising reacting fluorine, a Brønsted acid containing a conjugate base except for halides, and a pyridine compound in a reaction solvent, said pyridine compound having the general formula:

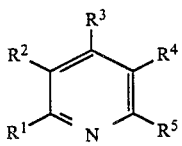

wherein:
(a) $R^1$ through $R^5$ are each a group selected from the class consisting of hydrogen, halogen, and methyl;
(b) when at least two of each of $R^1$ through $R^5$ are hydrogen, then the remaining one through three groups of $R^1$ through $R^5$ can each be selected from the class consisting of:
phenylcarbonyloxy substituted methyl,
a mixture of at least one fluoro substitutedmethyl group and at least one group selected from the class consisting of methyl, trifluoromethyl and halogen, and
alkyl containing two through four carbon atoms, provided that when each of two of $R^1$ through $R^5$ are tertiary butyl, said tertiary butyl groups are not adjacent; and
(c) when at least three of $R^1$ through $R^5$ are each hydrogen, then the remaining one or two groups of $R^1$ through $R^5$ can each be selected from the class consisting of:
phenyl,
acetyl,
alkoxycarbonyl containing a total of 2 through 4 carbon atoms wherein said alkyl substituent contains a total of 1 through 4 carbon atoms,
nitro,
cyano,
alkoxy containing 1 through 10 carbon atoms, and acyloxy wherein said acyl group contains 1 through 4 carbon atoms;
(d) when $R^3$ is hydrogen, then $R^1$ and $R^2$ taken together and $R^4$ and $R^5$ taken together can each form a six-membered carbocyclic ring which is inclusive of two adjacent carbon atoms of the pyridine ring; and
(e) when $R^3$ through $R^5$ are each hydrogen, then $R^1$ and $R^2$ taken together can form a five-membered heterocyclic ring which contains one oxygen atom, which is inclusive of two carbon atoms of the pyridine ring, and which has an oxo oxygen atom substituted on each ring carbon atom adjacent said ring oxy oxygen atom.

4. The process of claim 3 wherein said reaction solvent is selected from the class consisting of acetonitrile, methylene chloride, chloroform, tri-chloromethane, trichlorofluoromethane, trichlorotrifluoromethane, ethyl acetate, diethyl ether, tetrahydrofuran and mixtures thereof at a temperature in the range of about −100° C. to about 40° C., while maintaining the molar ratio of said Brønsted acid to said pyridine compound at least about 1:1, and wherein the molar ratio of said fluorine to said pyridine compound is at least about 1:1.

5. The process of claim 3 wherein said Brønsted acid conjugate base is selected from the class consisting of:

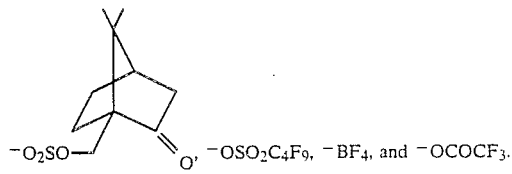

* * * * *

UNITED STATES PATENT AND TRADEMARK OFFICE
CERTIFICATE OF CORRECTION

PATENT NO.  :  4,996,320
DATED       :  February 26, 1991
INVENTOR(S) :  Umemoto et al.

It is certified that error appears in the above-identified patent and that said Letters Patent is hereby corrected as shown below:

On the Title Page, the designation of Assignee should also include Onoda Cement Company, Ltd.

In the Abstract, line 2, change "Bronsted" to --Brønsted--.

Column 1, line 6, after "Mar. 5" insert --,--.

Column 3, line 7, change "Bronsted" to --Brønsted--.

Column 3, line 25, change "Bronsted" to --Brønsted--.

Column 4, line 10, change "Brøsted" to --Brønsted--.

Column 4, line 23, change "p-sytrenesulfonic" to --p-styrenesulfonic"--;

Column 4, line 43, change "Brøsted" to --Brønsted--.

Column 4, line 45, change "Brøsted" to --Brønsted--.

UNITED STATES PATENT AND TRADEMARK OFFICE
CERTIFICATE OF CORRECTION

PATENT NO. : 4,996,320
DATED : February 26, 1991
INVENTOR(S) : Umemoto et al.

It is certified that error appears in the above-identified patent and that said Letters Patent is hereby corrected as shown below:

Column 4, line 47, change "Brøsted" to --Brønsted--.

Column 4, line 55, change "Brøsted" to --Brønsted--.

Column 5, line 13, change "Brøsted" to --Brønsted--.

Column 5, line 31, change "sue" to --use--.

Column 5, line 66, change "tri(tgrifluoroacetoxy)boron" to --tri(trifluoroacetoxy(boron)--.

Column 6, line 10, change "tot he" to --to the--.

Columns 25-26, Table 6, in the Heading, change "N-fluoropyridinum" to --N-Fluoropyridinium--.

Column 29, Table 7, in the Heading, change "N-Fluoropyridinum" to --N-Fluoropyridinium--.

Column 31, Table 7, in the Heading, change "N-Fluoropyridinum" to --N-Fluoropyridinium--.

UNITED STATES PATENT AND TRADEMARK OFFICE
CERTIFICATE OF CORRECTION

PATENT NO. : 4,996,320

DATED : February 26, 1991

INVENTOR(S) : Umemoto et al.

It is certified that error appears in the above-identified patent and that said Letters Patent is hereby corrected as shown below:

Column 33, Table 7, in the Heading, change
"N-Fluoropyridinum" to --N-Fluoropyridinium--.

Column 35, Table 8, in the Heading, change
"N-Fluoropyridinum" to --N-Fluoropyridinium--.

Column 37, Table 8, in the Heading, change
"N-Fluoropyridinum" to --N-Fluoropyridinium--.

Column 39, Table 8, in the Heading, change
"N-Fluoropyridinum" to --N-Fluoropyridinium--.

Column 41, Table 8, in the Heading, change
"N-Fluoropyridinum" to --N-Fluoropyridinium--.

Column 43, Table 8, in the Heading, change
"N-Fluoropyridinum" to --N-Fluoropyridinium--.

Column 45, Table 8, in the Heading, change
"N-Fluoropyridinum" to --N-Fluoropyridinium--.

UNITED STATES PATENT AND TRADEMARK OFFICE
CERTIFICATE OF CORRECTION

PATENT NO. : 4,996,320

DATED : February 26, 1991

INVENTOR(S) : Umemoto et al.

It is certified that error appears in the above-identified patent and that said Letters Patent is hereby corrected as shown below:

```
Column 47, Table 9, in the Heading, change
        "H-Fluoropyridnum" to  --N-Fluoropyridinium--.

Column 49, Table 10, in the Heading, change
        "H-Fluoropyridinum" to --N-Fluoropyridinium--.

Column 51, Table 10, in the Heading, change
        "H-Fluoropyridinum" to --N-Fluoropyridinium--.

Column 53, line 61, change "Brøsted" to --Brønsted--.

Column 55, line 11, change "Brøsted" to --Brønsted--.
```

Signed and Sealed this

Fifteenth Day of September, 1992

Attest:

DOUGLAS B. COMER

*Attesting Officer*  *Acting Commissioner of Patents and Trademarks*

UNITED STATES PATENT AND TRADEMARK OFFICE
CERTIFICATE OF CORRECTION

PATENT NO. : 4,996,320

DATED : February 26, 1991

INVENTOR(S) : Teruo Umemoto et al.

It is certified that error appears in the above-identified patent and that said Letters Patent is hereby corrected as shown below:

| | | |
|---|---|---|
| Cover page; [75] under "Inventors" | Hon; Ginjiro Tomizawa, | Tokyo; Ginjiro Tomizawa, |
| Column 6; line 23 | $-100+40°C$ | $-100$ to $+40°C$ |
| Column 6; line 24 | $-90+°C$ | $-90$ to $+20°C$ |
| Column 9; EX.12 | 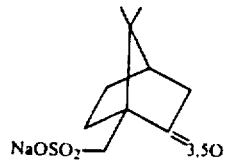 | 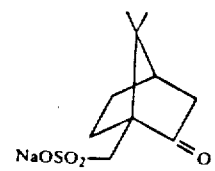 |
| Column 15; below EX.38 | | EXAMPLE 39 |
| Column 22; line 39 | $BD_3$ | $BF_3$ |

UNITED STATES PATENT AND TRADEMARK OFFICE
CERTIFICATE OF CORRECTION

PATENT NO. : 4,996,320        Page 2 of 5
DATED : February 26, 1991
INVENTOR(S) : Teruo Umemoto et al.

It is certified that error appears in the above-identified patent and that said Letters Patent is hereby corrected as shown below:

Column 23; last line (*) Measuring solvent is deuterated methanol.

|  |  |  |  |  |  |
|---|---|---|---|---|---|
|  | 208-209 | -52.67 (1F,bs,NF) | 169 | 23.62 1.11 5.44 |  |
| Columns 25-26; (Table 6-continued) EX.65 | | 150.5 (4F,s,BF$_4$) | 167(M$^+$-HBF$_4$) 165 | 23.62 1.11 5.44 | |
|  |  | 208-209 | -52.67 (1F,bs,NF) | 169 | |
|  |  |  |  | 167(M$^+$-HBF$_4$) | 23.62 1.11 5.44 |
|  |  | 150.5 (4F,s,BF$_4$) | | 165 | (23.66) (1.19) (5.52) |

Column 28; (Compound) NO.15

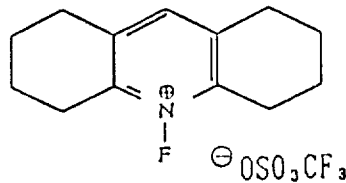 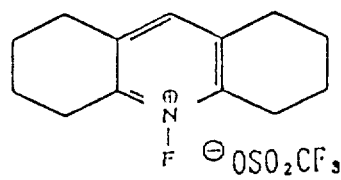

Column 39; EX.104

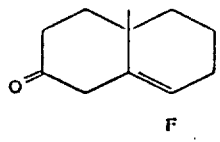 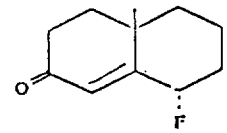

UNITED STATES PATENT AND TRADEMARK OFFICE
CERTIFICATE OF CORRECTION

PATENT NO. : 4,996,320

DATED : February 26, 1991

INVENTOR(S) : Teruo Umemoto et al.

It is certified that error appears in the above-identified patent and that said Letters Patent is hereby corrected as shown below:

11) Column 40; EX. 105

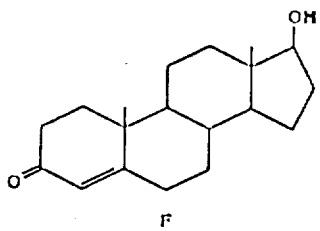 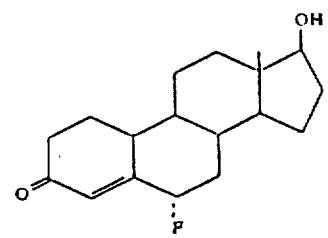

12) Column 42; EX. 107

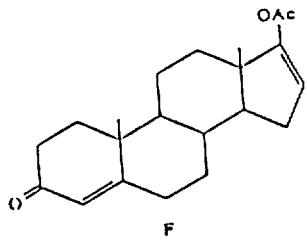 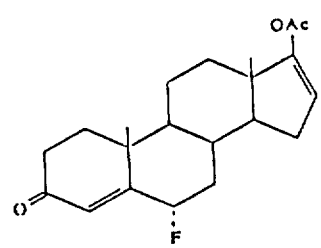

13) Column 43 EX. 108

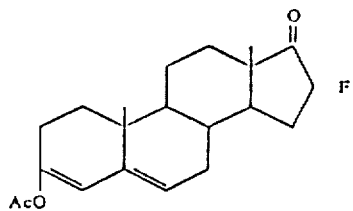 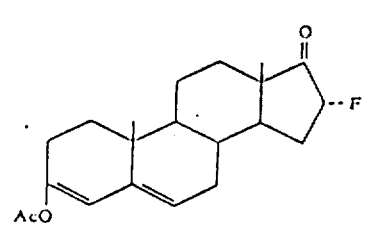

UNITED STATES PATENT AND TRADEMARK OFFICE
CERTIFICATE OF CORRECTION

PATENT NO. : 4,996,320          Page 4 of 5

DATED : February 26, 1991

INVENTOR(S) : Teruo Umemoto et al.

It is certified that error appears in the above-identified patent and that said Letters Patent is hereby corrected as shown below:

Column 50;
EX.127

$$\left.\begin{array}{c}\text{PhCHFSCH}_3 \ 4 \\ \vdots \\ \text{PhCH}_2\text{SCH}_2\text{F} \ 3\end{array}\right\} \qquad \left.\begin{array}{c}\text{PhCHFSCH}_3 \ 4 \\ \vdots \\ \text{PhCH}_2\text{SCH}_2\text{F} \ 3\end{array}\right\}$$

Column 50;
EX.128

$$\left.\begin{array}{c}\text{PhCHFSCH}_3 \ 4 \\ \vdots \\ \text{PhCH}_2\text{SCH}_2\text{F} \ 3\end{array}\right\} \qquad \left.\begin{array}{c}\text{PhCHFSCH}_3 \ 4 \\ \vdots \\ \text{PhCH}_2\text{SCH}_2\text{F} \ 3\end{array}\right\}$$

Column 20;
EX.49
Product

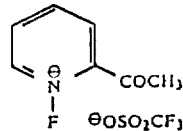 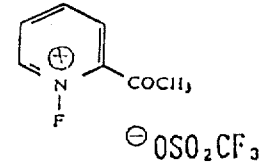

UNITED STATES PATENT AND TRADEMARK OFFICE
CERTIFICATE OF CORRECTION

PATENT NO. : 4,996,320  Page 5 of 5
DATED : February 26, 1991
INVENTOR(S) : Teruo Umemoto et al.

It is certified that error appears in the above-identified patent and that said Letters Patent is hereby corrected as shown below:

Columns 13 and 14; below Ex. 26

Example 27

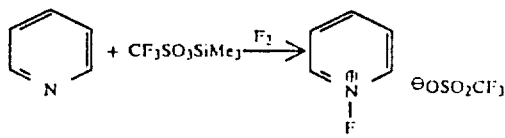

---

EXAMPLE 27

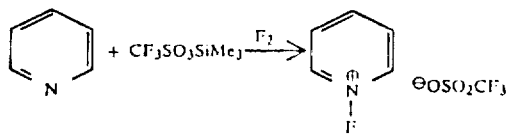

Signed and Sealed this

Twenty-first Day of December, 1993

Attest:

BRUCE LEHMAN

Attesting Officer     Commissioner of Patents and Trademarks